(12) United States Patent
Ying (10) Patent No.: US 9,078,569 B2
(45) Date of Patent: Jul. 14, 2015

(54) CONFIGURABLE DATA MEASUREMENT AND ACQUISITION SYSTEMS FOR MULTI-SLICE X-RAY COMPUTED TOMOGRAPHY SYSTEMS

(76) Inventor: Zhengrong Ying, Belmont, MA (US)

(*) Notice: Subject to any disclaimer, the term of this patent is extended or adjusted under 35 U.S.C. 154(b) by 276 days.

(21) Appl. No.: 13/589,245

(22) Filed: Aug. 20, 2012

(65) Prior Publication Data

US 2014/0050296 A1 Feb. 20, 2014

(51) Int. Cl.
| | |
|---|---|
| *G01N 23/00* | (2006.01) |
| *A61B 6/03* | (2006.01) |
| *A61B 6/00* | (2006.01) |
| *H05G 1/60* | (2006.01) |
| *G01N 23/083* | (2006.01) |

(52) U.S. Cl.
CPC .............. *A61B 6/032* (2013.01); *A61B 6/4225* (2013.01); *A61B 6/4291* (2013.01); *G01N 23/083* (2013.01); *H05G 1/60* (2013.01)

(58) Field of Classification Search
CPC ...... A61B 6/027; A61B 6/032; A61B 6/4291; A61B 6/4233; A61B 6/4085; A61B 6/4225; C07C 7/13; G01T 1/2018; G01T 1/2985
USPC ............ 378/4, 7, 15, 19, 21, 62, 64, 91, 98.8, 378/154, 174, 186; 250/363.05, 363.08, 250/370.09, 370.11, 394
See application file for complete search history.

(56) References Cited

U.S. PATENT DOCUMENTS

| | | | | | |
|---|---|---|---|---|---|
| 5,145,397 | A | * | 9/1992 | Yamada et al. | ............... 439/328 |
| 5,482,477 | A | * | 1/1996 | Michael | ........................ 439/581 |
| 5,947,753 | A | * | 9/1999 | Chapman et al. | ............... 439/79 |
| 6,081,576 | A | | 6/2000 | Schanen | |
| 6,115,448 | A | * | 9/2000 | Hoffman | ........................ 378/19 |
| 6,198,791 | B1 | | 3/2001 | He | |
| 6,235,993 | B1 | | 5/2001 | Johnston | |
| 6,522,715 | B2 | | 2/2003 | Hoffman | |
| 6,778,637 | B2 | | 8/2004 | Luhta | |
| 6,982,423 | B2 | | 1/2006 | Elgali | |
| 7,177,387 | B2 | | 2/2007 | Yasunaga | |
| 7,582,879 | B2 | | 9/2009 | Abenaim | |
| 7,606,346 | B2 | | 10/2009 | Tkaczyk | |
| 2002/0079458 | A1 | * | 6/2002 | Zur | ........................ 250/370.11 |
| 2006/0233298 | A1 | * | 10/2006 | Igarashi et al. | ................. 378/19 |
| 2007/0034807 | A1 | * | 2/2007 | Danzer et al. | ............ 250/370.11 |
| 2007/0086561 | A1 | * | 4/2007 | Bruder et al. | ...................... 378/7 |
| 2008/0165921 | A1 | * | 7/2008 | Tkaczyk et al. | ................ 378/19 |
| 2008/0285706 | A1 | * | 11/2008 | Schlomka | ........................ 378/6 |
| 2009/0238324 | A1 | * | 9/2009 | Oikawa | .............................. 378/7 |
| 2009/0245456 | A1 | * | 10/2009 | Tischenko et al. | ................ 378/4 |

OTHER PUBLICATIONS

Brock et al., Novel 3-D Coaxial Interconnect System for Use in System-in-Package Applications, Feb. 2000, IEEE Transactions on advanced packaging, vol. 33, No. 1, p. 37.*

* cited by examiner

*Primary Examiner* — Irakli Kiknadze
*Assistant Examiner* — Julio M Duarte-Carvajalino (57) ABSTRACT

A Data Measurement and Acquisition System (DMAS) for multi-slice X-ray CT systems and multi-slice X-ray CT systems using the DMAS are disclosed; wherein the DMAS comprises a plurality of X-ray scintillators, a plurality of photodiode modules, a plurality of digitizing cards, one or more motherboards, and an arced support structure for mounting and securing the photodiode modules, the digitizing cards, and the motherboard(s); wherein the multi-slice X-ray CT systems comprises one or more X-ray sources, and one or more DMAS.

11 Claims, 10 Drawing Sheets

CONFIGURABLE DATA MEASUREMENT AND ACQUISITION SYSTEMS FOR MULTI-SLICE X-RAY COMPUTED TOMOGRAPHY SYSTEMS

FIELD OF THE DISCLOSURE

The present disclosure relates to multi-slice X-ray Computed Tomography (CT) systems.

BACKGROUND

In X-ray CT systems, X-rays are used to image internal structure and features of a region of a subject or an object. The terms "subject" and "object" shall include anything capable of being imaged. The imaging is performed by an X-ray CT system, which images internal structure and features of a plurality of thin planar slices or a 3D volume of a region of an object using X-rays. For medical applications, the imaging objects include human bodies.

An X-ray CT system generally comprises an X-ray source that provides a cone-shaped X-ray beam and an array of closely spaced X-ray detectors that face the X-ray source. The X-ray source and array of detectors are mounted in a gantry so that a patient being imaged with the CT system, generally lying on an appropriate support couch, can be positioned within the gantry between the X-ray source and the array of detectors. The gantry and couch are moveable relative to each other so that the X-ray source and detector array can be positioned axially at desired locations along the patient's body.

The gantry comprises a stationary structure referred to as a stator and a rotary element referred to as a rotor, which is mounted to the stator so that the rotor is rotatable about the axial direction. In third generation CT systems, the X-ray source and detectors are mounted on the rotor. Angular positions of the rotor about the axial direction are controllable so that the X-ray source can be positioned at desired angles, referred to as view angles, around a patient's body.

To image a slice in a region of a patient's body, the X-ray source is positioned at the axial position of the slice and the X-ray source is rotated around the slice to illuminate the slice with X-rays from a plurality of different view angles. At each view angle, detectors in the array of detectors generate signals responsive to the intensity of X-rays from the source that pass through the slice. The signals are processed to determine amounts, by which X-rays from the X-ray source are attenuated over various path lengths through the slice that the X-rays traverse, in passing though the slice from the X-ray source to the detectors. The amounts, by which the X-rays are attenuated, are used to determine an X-ray absorption coefficient of materials in the slice as a function of position in the slice. The absorption coefficient is used to generate an image of the slice and identify compositions and densities of tissues in the slice.

The X-ray detectors comprised in a detector array of CT system are generally packaged in a plurality of modules, hereinafter referred to as CT detector-modules, each of which comprises a plurality of X-ray detectors. Most modern CT systems are multi-slice CT systems designed to simultaneously image a plurality of slices of a patient. The X-ray detectors in each CT detector-module of a multi-slice scanner are arranged in a rectangular matrix of rows and columns. The X-ray detector matrices of any two CT detector-modules in a CT system are substantially identical and comprise a same number of rows of detectors and a same number of columns of detectors. The modules are positioned one adjacent to and contiguous with the other in a closely packed array with their rows of detectors aligned end to end so that the X-ray detectors form a plurality of long parallel rows of X-ray detectors.

A multi-slice X-ray CT system is usually named or featured by the maximum number of slices that it can simultaneously image, for example, an 8-slice CT system means that it can simultaneously image at most 8 slices; a 16-slice CT system can simultaneously image at most 16 slices.

The X-ray detectors in each long row of detectors lie on an arc of a circle having its center located at a focal point of the CT system's X-ray source, and the design of these detectors is specifically determined by the radius of the circle, which is hereinafter referred to as focusing distance. The design of X-ray detectors placed on the arc of one focusing distance of one CT system cannot therefore be used on another CT system of a different focusing distance.

X-ray detectors typically include a collimator having a plurality of anti-scatter plates for collimating x-ray beams received at the detector, a scintillator for converting x-rays to light energy adjacent the collimator, and photodiodes for receiving the light energy from the adjacent scintillator and producing electric charges therefrom. The anti-scatter plates of a collimator are aligned and bounded with the elements of the scintillator arrays to very tight and exact tolerances. This alignment and bounding of the plurality of elements of the scintillator array and the anti-scatter plates of the collimator can be a time consuming and a labor intensive process.

Electronic components for processing analog signals from the X-ray detectors in a CT detector-module are usually located at positions removed from the detector module. Each detector in a detector module is connected to the module's electronic processing components via a cable over which analog signals from the detector are transmitted to the processing electronics. Because the electric charges produced by the photodiodes are extremely small, the cables carrying these small charges are very susceptible to interferences, resulting in artifacts in reconstructed CT images; the longer the cables are, the more interferences they are exposed to.

SUMMARY OF THE DISCLOSURE

In accordance with one embodiment of the present disclosure, a Data Measurement and Acquisition System (DMAS) for multi-slice X-ray Computed Tomography (CT) systems, wherein each of the X-ray CT systems may include at least one X-ray source, comprises a plurality of X-ray scintillator arrays for receiving and converting X-ray photons to light photons; a plurality of photodiode modules with the X-ray scintillator arrays being mounted on for converting the light photons to analog signals; a plurality of digitizing cards connected with the photodiode modules for digitizing the analog signals into digital data; one or more motherboards connected with the digitizing cards using digital cables, wherein the motherboards control the digitizing cards for sampling and digitizing the analog signals; and an arced support structure for mounting and securing the photodiode modules, the digitizing cards, and the motherboards; wherein the arc of the arced support structure focuses on one X-ray source of the X-ray CT system and each X-ray scintillator array is configured and arranged to focus on the X-ray source.

In one embodiment of the present disclosure, the DMAS can be arranged and configured for multi-slice X-ray CT systems of different X-ray source focusing distances; and wherein the arced support structure of the DMAS is fabricated from an arced casting of a first radius that is within a pre-determined range of radii and is then machined to a second radius that is within the pre-determined range of radii;

wherein the first radius and the second radius are different; and wherein the X-ray source focusing distances are the radii of the arced support structure. This process allows a range of arced support structure to be fabricated from one casting, which is costly to produce, reducing the total cost for manufacturing the arced support structures of different radii.

In one embodiment of the present disclosure, the DMAS includes anti-scatter plates and curved anti-scatter toothed metal strips; wherein the anti-scatter plates are secured and aligned with the scintillator arrays using the curved anti-scatter toothed metal strips; wherein the curved anti-scatter toothed metal strips are aligned and secured to the arced support structure of the DMAS. The curved anti-scatter toothed metal strips are made of flexible metal or other suitable substance; wherein each of two opposite sides of each anti-scatter plate communicates with precise slots of at least two curved anti-scatter toothed metal strips that are aligned along Y-axis; wherein the curved anti-scatter toothed metal strips assume the same radius as the arced support structure; and wherein the combination of the radius and the precise slots align the anti-scatter plates to the X-ray source. The use of the curved anti-scatter toothed metal strips for securing and aligning the anti-scatter plates offers a cost-saving and efficient way compared with bonding the anti-scatter plates on to the scintillator arrays.

In one embodiment of the present disclosure, each photodiode module may include a photodiode array for converting light photons to analog signals, and a support substrate, to which the photodiode array is precisely mounted; and wherein the support substrate may include a support plate mounted to the support substrate structure on the opposite side that the photodiode array is mounted to. The support plate strengthens the support substrate so that low-cost support substrate materials and manufacturing processes can be used to lower the total cost of the photodiode module but still achieving satisfactory rigidity and thermal expansion requirements.

In accordance with one embodiment of the present disclosure, each photodiode module may include one or more high-density connectors, a photodiode array and a support substrate; wherein the photodiode array is precisely mounted to the support substrate; wherein the high-density connectors are precisely mounted to the support substrate; and wherein the analog signals generated by the photodiode array are transported to the high-density connectors. Using high-density connectors instead of traditional flexible cables reduces the total length of the transportation of the analog signals, which is extremely susceptible to interference, for reducing the interference.

In accordance with one embodiment of the present disclosure, each digitizing card further includes a high-density plug corresponding to one of the high-density connectors of the photodiode modules. The high-density connectors on the support substrate of each photodiode module have different mated heights along Y-axis. The high-density connectors are displaced along Z-axis. The digitizing cards connecting each photodiode module are displaced along Y-axis. This configuration allows to pack and to arrange the photodiode modules and digitizing cards in a very space saving manner.

In accordance with one embodiment of the present disclosure, a multi-slice X-ray Computed Tomography (CT) system comprises one or more X-ray sources and one or more Data Measurement and Acquisition Systems (DMAS) of the present disclosure. The DMAS can be configured with different number of digitizing cards, resulting in different multi-slice X-ray CT systems of different slice numbers.

BRIEF DESCRIPTION OF THE DRAWINGS

The drawing figures depict embodiments by way of example, not by way of limitations. In the figures, like reference numerals refer to the same or similar elements.

DETAILED DESCRIPTION OF THE DRAWINGS

Figure 1:
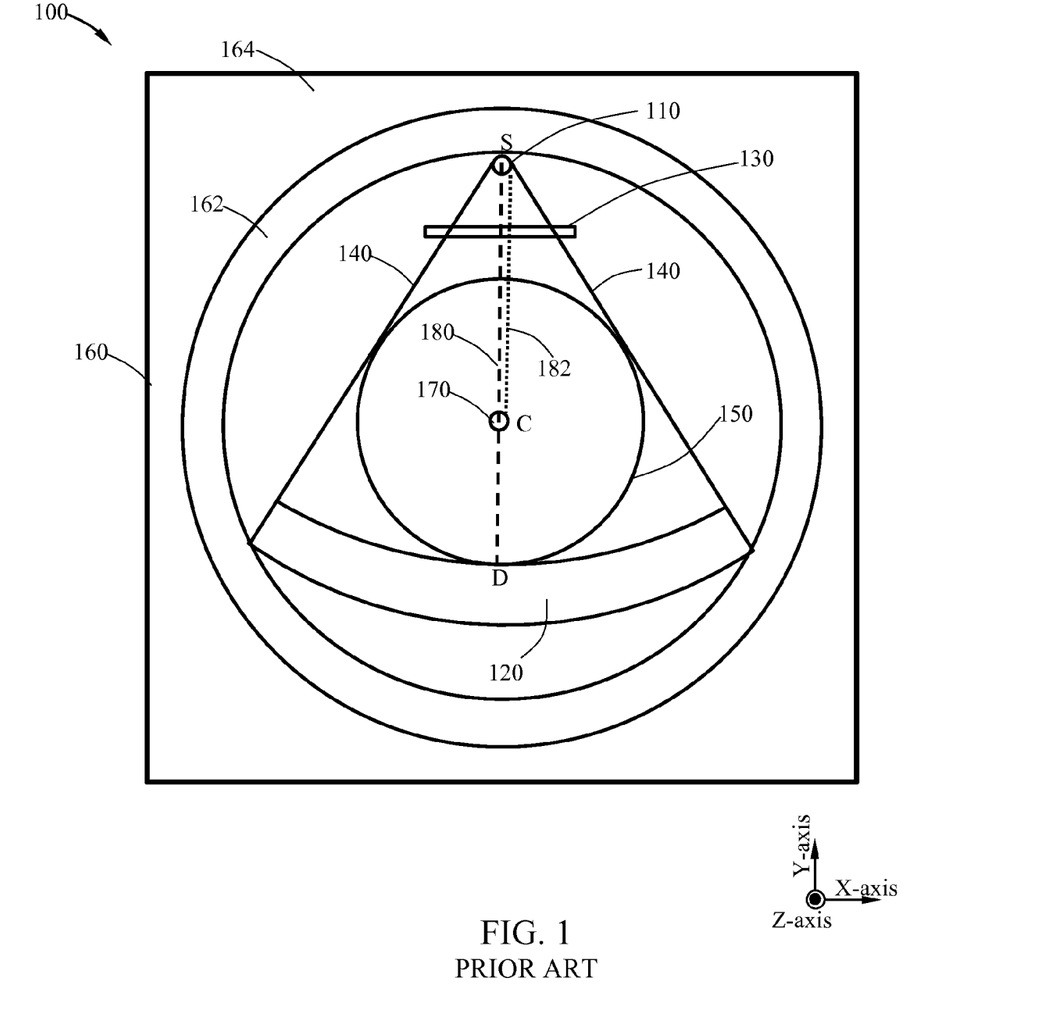
FIG. 1 shows a schematic functional diagram of a prior art multi-slice X-ray CT system.

FIG. 1 shows a schematic functional diagram of a prior art multi-slice X-ray CT system 100. A conventional multi-slice CT system typically comprises an X-ray source 110, which generates a cone-shaped X-ray beam 140. The X-ray beam 140 passes through a pre-patient collimator 130, which allows X-ray beam to illuminate only the targeted area and blocks X-ray beam in unwanted area. A patient usually lies down within the scanner's scanning Field Of View (FOV) 150, where the X-ray beam 140 illuminates. The X-ray detector system 120 receives X-ray photons and converts to analog signals that proportional to X-ray photon energies. The X-ray CT system 100 also comprises a gantry 160, which includes a rotational part 162 and a stationary part 164. The X-ray source 110, the collimator 130 and the detector system 120 are mounted on the rotational part 162 of the gantry 160. The rotational part 162 rotates around the rotation center 170.

The distance 182 between the focal spot S of the X-ray source 110 and the rotation center, or iso-center, C is hereinafter referred to as Rsc, and the distance 180 between the focal spot S of the X-ray source 110 and the detector system D is hereinafter referred to as focusing distance Rsd. Different CT systems may have different Rsc, Rsd, or scanning FOV.

The direction from the iso-center or rotation center to the focal spot of the X-ray source is hereinafter referred to as Y-axis, and the direction perpendicular to the imaging plane or the rotation plane is hereinafter referred to as Z-axis, and the direction perpendicular to the Y-axis within the rotation plane is hereinafter referred to as X-axis.

Figure 2A:
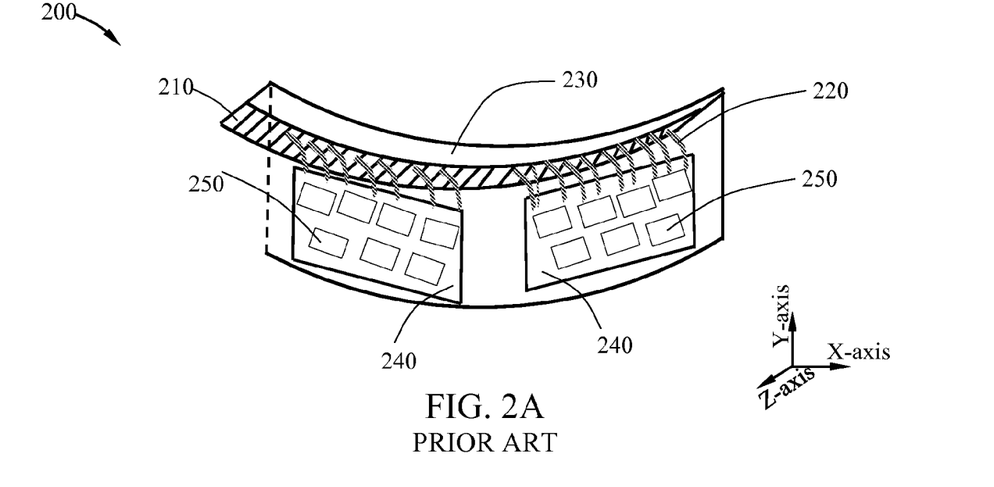
FIG. 2A shows a schematic functional diagram of a prior art CT detector array system.

FIG. 2A shows a schematic functional diagram of a prior art CT detector array system 200, like the detector array system 120 in the prior art CT system 100 of FIG. 1. The detector array system 200 typically comprises detector modules 210, analog data processing units 250, which reside on data control boards 240. Cables 220 connecting the detector modules 210 and data control boards 240, and pass the analog signal generated by detector modules 210 to data processing units 250 on the data control boards 240. The analog data processing units 250 are located removed from the detector modules 210. Because the electric charges produced by the detector modules are extremely small, the cables carrying these small charges are very susceptible to interferences, resulting in artifacts in reconstructed CT images; the longer the cables carrying the electric charges are, the more interferences they are exposed to.

The detector modules 210 are positioned one adjacent to and contiguous with the other in a closely packed array with their rows of detectors aligned end to end on a support structure 230. The arc-shaped support structure 230 has its center located at a focal point of the CT system's X-ray source. The radius of the prior art arc-shaped support structure is fixed and is designed for a particular CT system model, so are the detector modules.

Figure 2B:
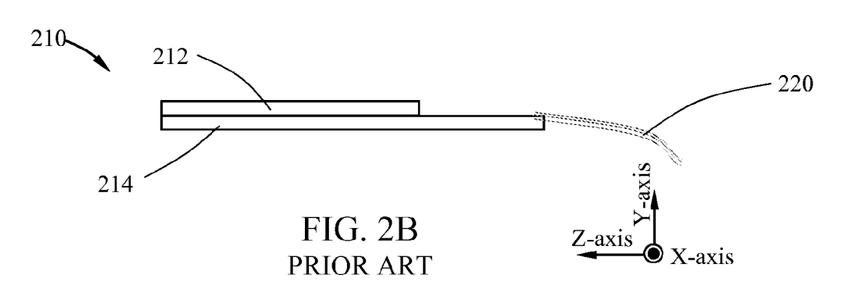
FIG. 2B shows a cross-sectional view of a schematic functional diagram of a prior art detector module used in the prior art CT detector array system of FIG. 2A.

FIG. 2B shows a cross-sectional view of a schematic functional diagram of a prior art detector module used in the prior art CT detector array system of FIG. 2A. Each detector module comprises a scintillator array 212 mounted on a photodiode module 214. The photodiode module 214 is then connected with flexible cable 220 to pass the analog signals to the data processing units 250 on the data control boards 240.

Figure 2C:
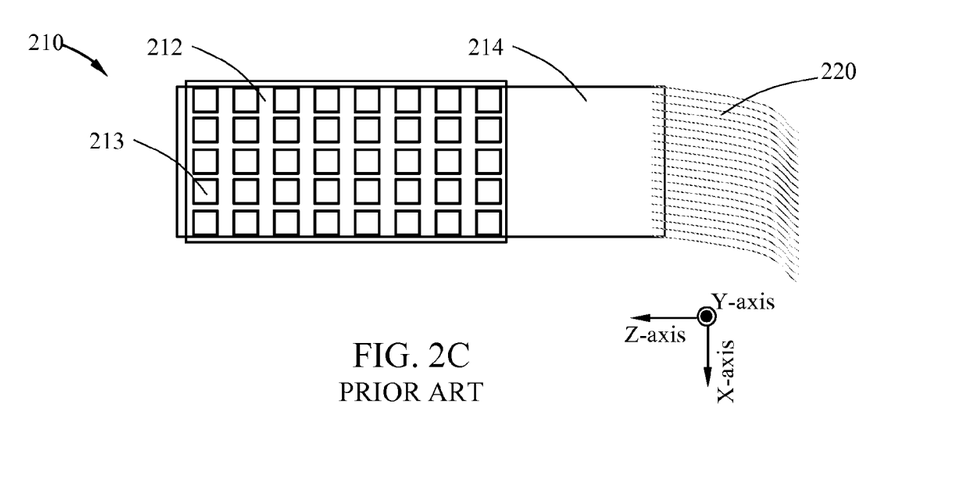
FIG. 2C shows a top view of a schematic functional diagram of the prior art detector module of FIG. 2B.

FIG. 2C shows a top view of a schematic functional diagram of the prior art detector module of FIG. 2B. The scintillator array 212 comprises a matrix of scintillator element 213. The matrix is composed of a number of rows along the Z-axis and a number of columns along the X-axis. For example, for an 8-slice CT scanner, the number of rows is 8, and the number of columns is 16.

Figure 3:
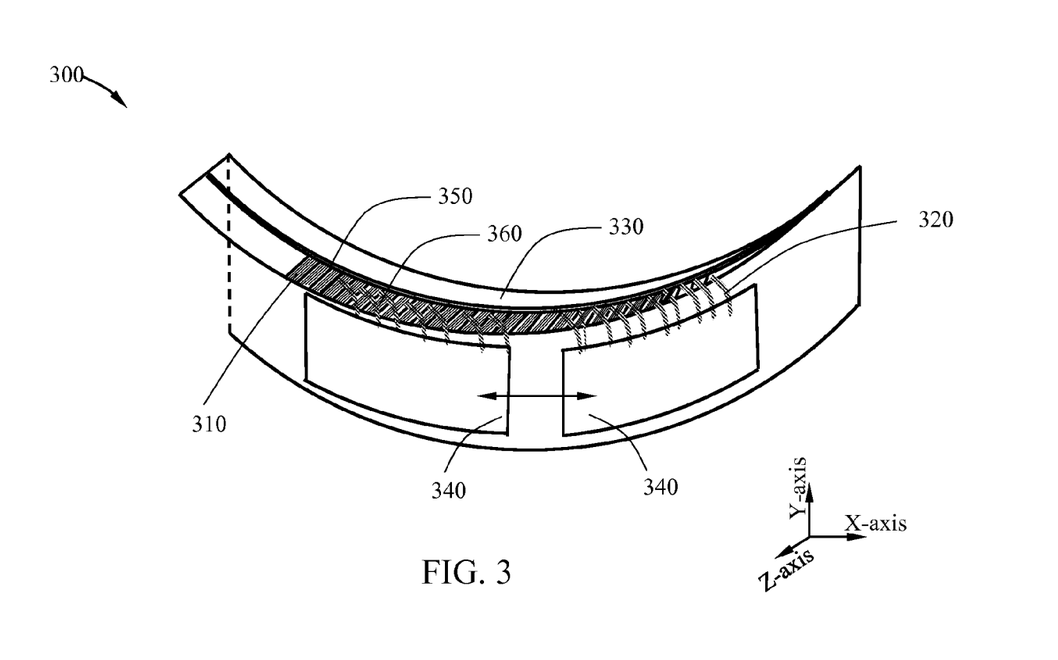
FIG. 3 shows a schematic functional diagram of a multi-slice X-ray CT data measurement and acquisition system (DMAS) in accordance with one embodiment of the present disclosure.

FIG. 3 shows a schematic functional diagram of a multi-slice X-ray CT Data Measurement and Acquisition System (DMAS) 300 of one embodiment of the present disclosure. In accordance with one aspect of the embodiment of the present disclosure, the DMAS 300 comprises a plurality of DMAS modular assemblies 310, a plurality of digital cables 320, a DMAS arced support structure 330, one or more DMAS motherboards 340, one or more flexible curved anti-scatter toothed metal strips 350, and a plurality of anti-scatter plates 360.

In accordance with one embodiment of the present disclosure, the DMAS modular assemblies 310 receive and convert X-ray photons to digital data and transport the digital data through the digital cables 320 to DMAS motherboards 340. The motherboards 340 assemble the digital data according to the ordering of the DMAS modular assemblies and transfer the digital data to a reconstruction engine of the X-ray CT system for generating CT images of a scanned object. The motherboards 340 also control DMAS modular assemblies to sample and digitize the received X-ray photons, for example, sampling start time, integration time, digitizing resolution, resetting, self-diagnosis, and power-up self-test. The DMAS arced support structure 330 assembles all the DMAS modular assemblies 310 to form an arc that centers at the X-ray source. The anti-scatter plates 360 are secured by the curved anti-scatter toothed metal strips 350, blocking scattered X-ray photons and allowing only transmitted X-ray photons to reach DMAS modular assemblies. The curved anti-scatter toothed metal strips 350 are also mounted and secured along the arc of the DMAS arced support structure, hence the curved anti-scatter toothed metal strips have the same curvature as the arced support structure centered at the X-ray source.

Figure 4A:
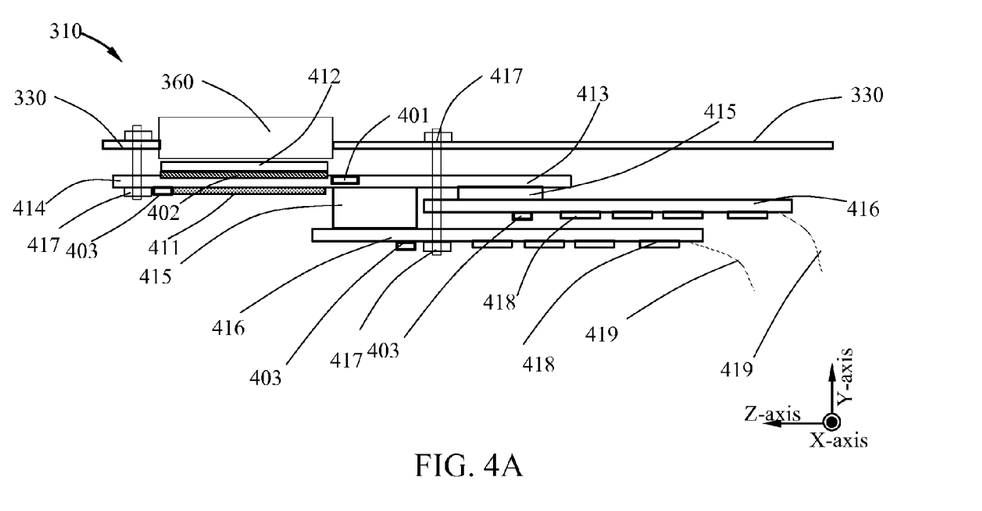
FIG. 4A shows a cross-sectional view of a DMAS modular assembly of the multi-slice X-ray CT DMAS in accordance with one embodiment of the present disclosure.
Figure 4B:
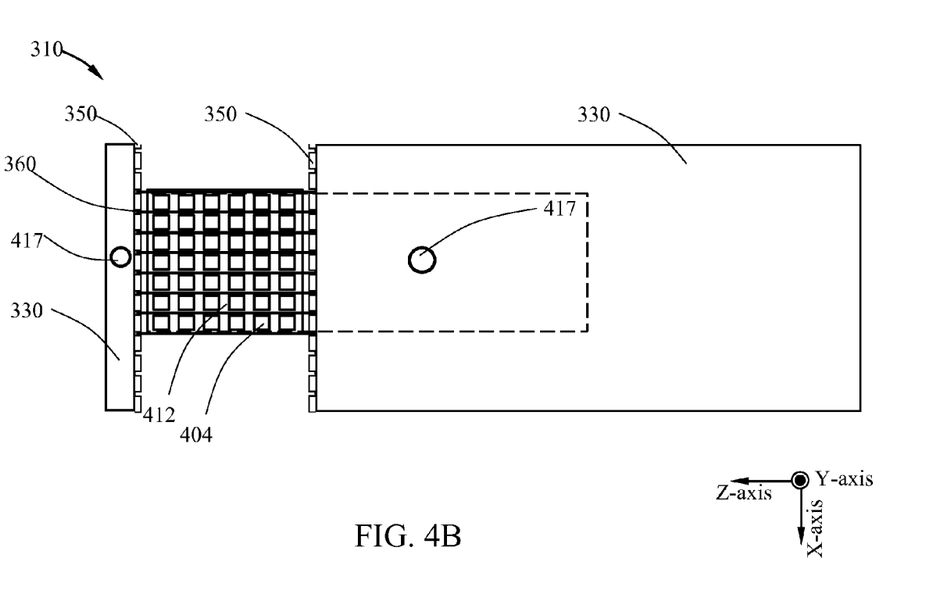
FIG. 4B shows a top view of the DMAS modular assembly of the multi-slice X-ray CT DMAS in accordance with one embodiment of the present disclosure.

FIG. 4A shows a cross-sectional view of a DMAS modular assembly 310 of the multi-slice X-ray CT DMAS 300 of one embodiment of the present disclosure. FIG. 4B shows a top view of the DMAS modular assembly 310 of the multi-slice X-ray CT DMAS 300 of one embodiment of the present disclosure.

Referring to FIG. 4A and FIG. 4B, in accordance with one embodiment of the present disclosure, the DMAS modular assembly 310 comprises a scintillator array 412, a photodiode module 414, one or more high-density connectors 415, one or more digitizing cards 416, one or more fasteners 417, and one or more digital cables 419.

Referring to FIG. 3, FIG. 4A and FIG. 4B, in accordance with one embodiment of the present disclosure, the DMAS 300 comprises a plurality of X-ray scintillator arrays 412 for receiving and converting X-ray photons to light photons; a plurality of photodiode modules 414 with the X-ray scintillator arrays 412 being mounted on for converting the light photons to analog signals; a plurality of digitizing cards 416 connected with the photodiode modules for digitizing the analog signals into digital data; one or more motherboards 340 connected with the digitizing cards 416 using digital cables 419; wherein the motherboards 340 control the digitizing cards 416 for sampling and digitizing the analog signals; and, an arced support structure 330 for mounting and securing the photodiode modules 414, the digitizing cards 416, and the motherboards 340; wherein the arc of the arced support structure focuses on one X-ray source of the multi-slice X-ray CT system and each X-ray scintillator array 412 is configured and arranged to focus on the X-ray source.

In one exemplary embodiment of the present disclosure, the scintillator array 412 converts X-ray photons to light photons. Examples of the materials used for constructing scintillator array include $Gd_2O_2S$, $CdWO_4$, and other scintillation crystals that can generate light photons when impinged by an x-ray beam. The scintillator array 412 comprises a matrix of scintillator elements 404 as shown in FIG. 4B. The direction along the Z-axis is called row direction, and the direction along X-axis is called column direction. An example of the scintillator matrix size is 16 rows by 32 columns. The scintillator elements are cut from the scintillator array, and each scintillator element is coated with light-retaining materials, for example, epoxy, to retain light photons within the scintillator element and to allow light photons to exit only on the interface to the photodiode module 414.

In another exemplary embodiment of the present disclosure, the scintillator array 412 is mounted on the photodiode module 414, which includes a photodiode array 402, a support substrate 413, and a plurality of combination Field Effect Transistor (FET) switches 401. The photodiode array 402 is precisely mounted to the support substrate 413. The support substrate 413 may also include a support plate 411 mounted to the support substrate 413 on the opposite side that the photodiode array 402 is mounted to. In one embodiment of the present disclosure, the support substrate 413 is made of Printed Circuit Board (PCB) materials, and the support plate 411 is made of ceramic. The PCB materials are easier and cheaper to be manufactured than ceramic for the support substrate, but it is not as rigid as ceramic and also has larger thermal expansion coefficient than ceramic. Using a ceramic support plate, which is much smaller than the support substrate, in combination with the PCB support substrate, the overall cost of the photodiode module is reduced while the rigidity of the module is maintained.

In accordance with one embodiment of the present disclosure, each scintillator element 404 of the scintillator array 412 is precisely mounted on each photodiode of the photodiode array 402 with light-transparent adhesive. Each photodiode converts the light photons transmitted from each scintillator element 404 to analog signals. In accordance with one aspect of the embodiment of the present disclosure, the support substrate 413 is made of very rigid materials that have small thermal expansion coefficient, for example, ceramic. The combination switches 401 combine the output analog signals of nearby two rows of photodiodes into one row of analog signals. For example, for a 32-row photodiode array, when the combination switches are enabled, the output of the photodiode array contains 16 rows of analog signals; when the combination switches are disabled, the photodiode array contains 32 rows of analog signals. The analog signals, or the electric charge converted by the photodiodes, are transported by wire traces in the substrate to high-density connectors 415 through the combination switch 401.

In one embodiment of the present disclosure, each photodiode module 414 includes one or more high-density connectors 415, a photodiode array 402 and a support substrate 413; wherein the photodiode array 402 is precisely mounted to the support substrate 413; wherein the high-density connectors 415 are precisely mounted to the support substrate 413 on the opposite side that the photodiode array 402 is mounted to; and wherein the analog signals generated by the photodiode array 402 are transported to the high-density connectors 415 directly.

According to one aspect of one embodiment of the present disclosure, the photodiode module 414 may include a temperature measuring sensor 403 for measuring the temperature of the photodiode module 414 and scintillator array 412, for example, a two-terminal or three-terminal or four-terminal platinum Resistance Temperature Detector (RTD). For a four-terminal platinum RTD, two terminals are used for supplying power to the RTD and the other two terminals are used for measurements.

According to another aspect of one embodiment of the present disclosure, the photodiode module 414 also includes one or more high-density connectors 415, for example, 400-position high-density connectors. The high-density connectors 415 allow digitizing cards 416 to connect with the substrate 413 of the photodiode module 414 without using flexible cables. Using the high-density connectors also shortens the length of the analog signals from photodiode array 402 to Analog to Digital Conversion (ADC) processing units 418 on the digitizing cards 416, resulting in much lower interference to the extremely weak analog signals.

Still referring to FIG. 4A, in one exemplary embodiment of the present disclosure, the photodiode module 414 includes two high-density connectors 415 that are displaced along the Z-axis. The two high-density connectors have different mated heights along the Y-axis. Each digitizing card includes one high-density plug corresponding to one of the high-density connectors 415 of the photodiode modules 414. Each of the high-density connectors is plugged in with one digitizing card 416, resulting in two digitizing cards for the DMAS modular assembly 310. The high-density connector 415 closer to the photodiode array 402 and scintillator array 412 has a larger mated height than the other high-density connector 415. The different mated heights of the two high-density connectors allow the two digitizing cards 416 to be displaced along the Y-axis with an offset along the Z-axis but aligned along the X-axis with the photodiode module 414 and scintillator array 412.

In one embodiment of the present disclosure, the digitizing card 416 comprises a plurality of ADC processing units 418. Each ADC processing unit is a high-precision multi-channel AD convertor. For medical applications, it typically requires 18-bit or more resolution; while for other applications, 12-bit resolution might be sufficient. For example, a single Integrated Circuit (IC) chip of 128-channel 24-bit resolution AD convertors is available on market, which can be used for X-ray CT systems of medical applications. The ADC processing units 418 converts the analog signals generated from the photodiode array 402 to digital data. Each channel of the digital data represents the X-ray intensity that each scintillator element receives. The digital data is transmitted through digital cable 419 to one of the DMAS motherboards 340 as shown in FIG. 3. In another aspect of the embodiment of the present disclosure, the digital cable 419 is shielded micro-coax cable. It is known to those skilled in the art that the digital data is much less susceptible to interference than analog signals, therefore using cables for transporting the digital data to the motherboards offer great advantages over using cables for transporting the analog signals to the motherboards. In addition, the number of wires required for transporting the analog signals is much larger than the number of wires required for transporting the digital data, for example, about 300 wires are required for transporting the analog signals of 256 channels of photodiode array; while for digital data, about 10 wires are needed for transporting the digital data of 256 channels of photodiode array.

In another embodiment of the present disclosure, the digitizing card 416 may also include a temperature measuring sensor 403 for measuring the temperature of digitizing card 416, for example, a two-terminal or three-terminal or four-terminal platinum Resistance Temperature Detector (RTD). For a four-terminal platinum RTD, two terminals are used for supplying power to the RTD and the other two terminals are used for measurements.

In accordance with one embodiment of the present disclosure, the digital cable may also transmit the signals of the temperature sensor 403 on the photodiode module 414 and on the digitizing card 416. For four-terminal RTDs, each RTD requires that three wires of power and signals be transmitted over the digital cable 419 to one of the DMAS motherboards 340.

Still referring to FIG. 4A and FIG. 4B, in accordance with one embodiment of the present disclosure, two fasteners 417 are used to secure and precisely align the photodiode module 414, and the digitizing cards 416 to the DMAS arced support structure 330. The fastener 417 left to the scintillator array 412 secures and aligns the photodiode module 414 to the DMAS arced support structure 330; the fastener 417 right to the scintillator array 412 secures and aligns the photodiode module 414 and digitizing cards 416 to the DMAS arced support structure 330.

Figure 4C:
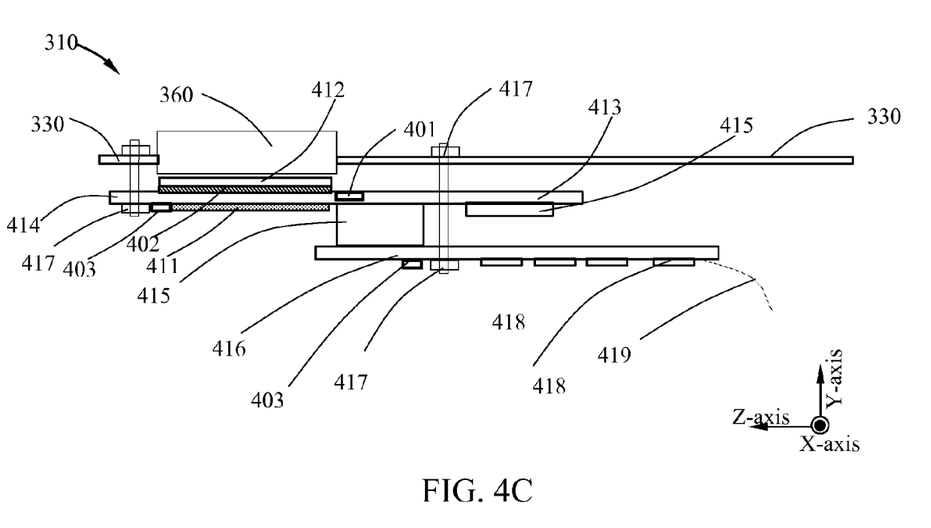
FIG. 4C shows a cross-sectional view of an alternative configuration of the modular assembly of the multi-slice X-ray CT DMAS in accordance with one embodiment of the present disclosure.

FIG. 4C shows a cross-sectional view of a DMAS modular assembly 310 of the multi-slice X-ray CT DMAS 300 of one embodiment of the present disclosure. In this alternative configuration, there is only one digitizing card 416 is plugged in to one of the two high-density connectors 415.

In accordance with one embodiment of the present disclosure, the DMAS 300 can be arranged and configured with a first number, for example 46, of digitizing cards for a first multi-slice X-ray CT system, for example 16-slice X-ray CT system; wherein the DMAS can also be arranged and configured with a second number, for example 92, of digitizing cards for a second multi-slice X-ray CT system, for example 32-slice X-ray CT system.

Referring to FIG. 4A, FIG. 4B, and FIG. 4C, in accordance with one embodiment of the present disclosure, the scintillator array 412 on each DMAS modular assembly 310 has a matrix of scintillator elements of 32 rows along Z-axis by 16 columns along X-axis, the photodiode module 414 also has the same matrix size as the scintillator array with 32 rows along Z-axis by 16 columns along X-axis, which is referred hereinafter as photodiode array. The output analog signals of center 16 rows (256 channels=16 center rows×16 columns) of the photodiode array 402 on the photodiode module 414 are wired to one of the high-density connector 415, and the outer 16 rows (256 channels=16 outer rows×16 columns) of the photodiode array 402 on the photodiode module 414 are wired to the other high-density connector 415.

In accordance with another embodiment of the present disclosure, all the output analog signals of the photodiode array 402 are first connected to the combination FET switch 401 of the photodiode module 414. When the combination FET switch 401 is disabled, that is, the switch is on a pass through mode, the analog signals of the inner 16 rows are connected with the one of the high-density connector 415, and the analog signals of the outer 16 rows are connected with the other high-density connector 415; when the combination FET switch 401 is enabled, that is, the switch combines the analog signals of two neighboring rows into one row analog signals, 32 rows of analog signals are combined into 16 rows of analog signals, and then routed and connected to one of the high-density connectors 415.

In accordance with one embodiment of the present disclosure, each photodiode module includes the combination switches for combining elements of photodiode modules along Z-axis when enabled and for passing through the analog signals only when disabled; wherein the DMAS can be arranged and configured with a first number, for example 46, of digitizing cards for a first multi-slice X-ray CT system, for example 16-slice X-ray CT system, and with the combination switches on the photodiode modules being enabled or being disabled; wherein the DMAS can also be arranged and configured with a second number, for example 92, of digitizing cards for a second multi-slice X-ray CT system, for example 32-slice X-ray CT system, and with the combination switches on the photodiode modules being disabled.

In accordance with one embodiment of the present disclosure, each digitizing card 416 converts 256 channels of analog signals into digital data. In one configuration of the DMAS modular assembly 310, there is only one digitizing card 416 connected with one of the two high-density connectors 415. In this configuration, the DMAS 300 acquires, converts, and outputs either inner 16 rows or combined 16 rows of analog signals. In another configuration, there are two digitizing cards 416 connected with both high-density connectors 415, the DMAS 300 acquires, converts, and outputs 32 rows of analog signals.

In accordance with one exemplary embodiment of the present disclosure, the DMAS 300 can be configured and used in, for example 16-slice X-ray CT systems, when there is only one digitizing card in each of the DMAS modular assembly; the DMAS 300 can also be configured and used in, for example, 32-slice X-ray CT systems, when there are two digitizing cards in each of the DMAS modular assembly. In accordance with another embodiment of the present disclosure, the DMAS 300 can be configured and used in, for example 32-slice X-ray CT systems, when there is only one digitizing card in each of the DMAS modular assembly with X-ray source of flying focal spot along Z direction; the DMAS 300 can also be configured and used in, for example 64-slice X-ray CT systems, when there are two digitizing cards in each of the DMAS modular assembly with X-ray source of flying focal spot along Z direction.

Figure 5A:
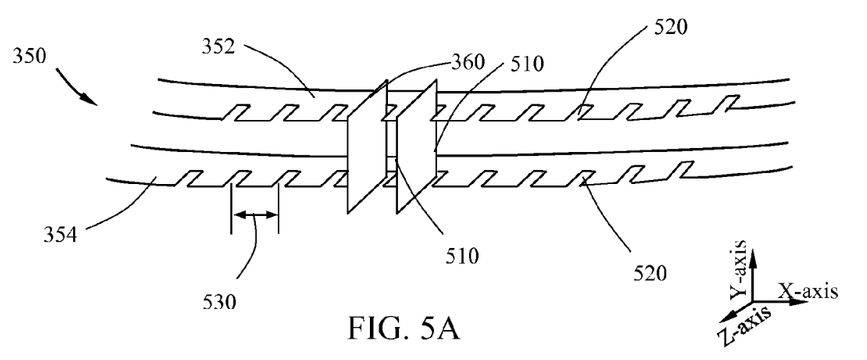
FIG. 5A shows a schematic functional diagram of anti-scatter plates assembled in curved anti-scatter toothed metal strips in accordance with one embodiment of the present disclosure.

Referring to FIG. 3, FIG. 4A, FIG. 4B, and FIG. 5A, in accordance with one embodiment of the present disclosure, anti-scatter plates 360 are placed perpendicular to the scintillator array 412 along Z-axis. Each anti-scatter plate is placed between two columns of the scintillator elements and each anti-scatter plate is aligned to the focal spot of the X-ray source as shown in FIG. 4B. Each anti-scatter plate 360 is not glued or bonded to the scintillator array, but rather is secured by the curved anti-scatter toothed metal strips 350 as shown in FIG. 5A. The curved anti-scatter toothed metal strips are secured and aligned using pre-set circular holes along the arc of the DMAS arced support structure, thus the curved anti-scatter toothed metal strips have the same curvature as the DMAS arced support structure. On each side of the opening of the DMAS arced support structure 330, there are two curved anti-scatter toothed metal strips with slots 520 aligned along the Y-axis, each anti-scatter plate 360 is placed and secured in the slots of the curved anti-scatter toothed metal strips. The anti-scatter plates are typically made of high atomic-number materials, for example, tungsten. The curved anti-scatter toothed metal strips can be made of stainless steel with slots being fabricated using etching technique. Each slot is, for example, 110 um wide, and each anti-scatter plate is, for example, 100 um thick. The curved anti-scatter toothed metal strips are secured and mounted along the DMAS arced support structure 330 as shown in FIG. 3.

Figure 5B:
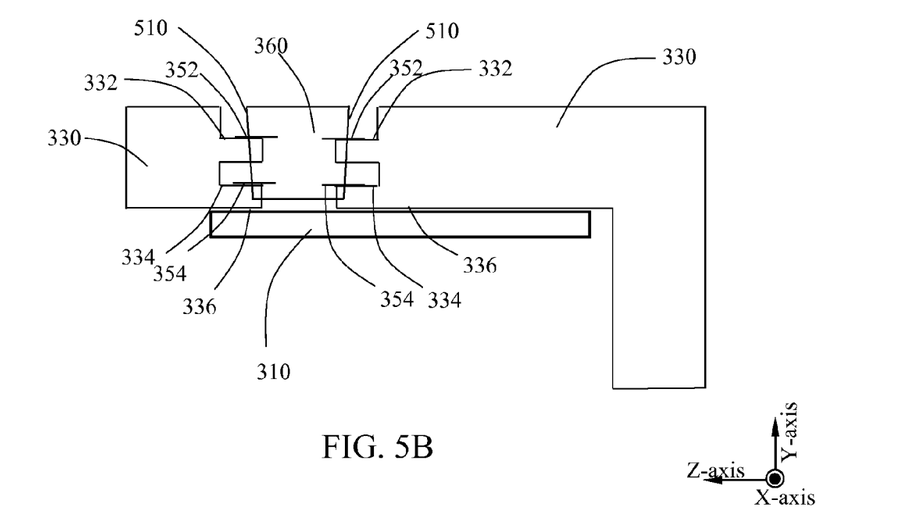
FIG. 5B shows a schematic functional diagram of cross-sectional view of anti-scatter plates assembled in curved anti-scatter toothed metal strips and an arced support structure in accordance with one embodiment of the present disclosure.

FIG. 5B shows a schematic functional diagram of cross-sectional view of anti-scatter plates 360 assembled in curved anti-scatter toothed metal strips 350 and an arced support structure 330 in accordance with one embodiment of the present disclosure. The arced support structure 330 includes an upper arced support structure 332 for supporting and securing the upper curved anti-scatter toothed metal strips 352, a lower arced support structure 334 for supporting and securing the lower curved anti-scatter toothed metal strips 354, and a chorded bottom 336 for securing and aligning the DMAS modular assemblies 310.

Figure 5C:
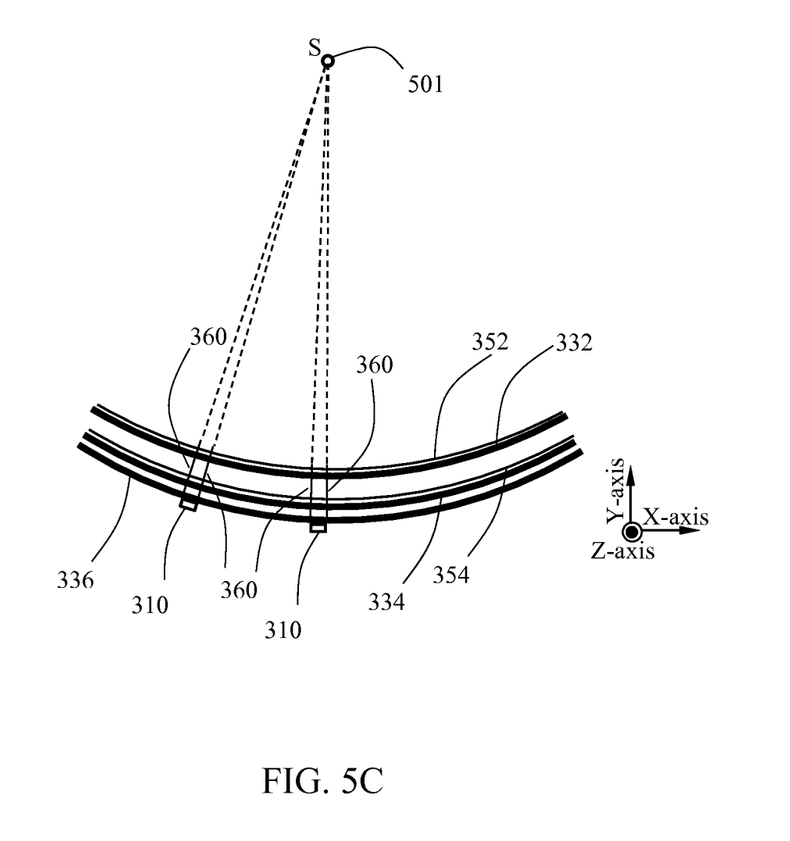
FIG. 5C shows a schematic functional diagram of an arced support structure for securing and aligning curved anti-scatter toothed metal strips in accordance with one embodiment of the present disclosure.

FIG. 5C shows a schematic functional diagram of the arced support structure for securing and aligning curved anti-scatter toothed metal strips 350 in accordance with one embodiment of the present disclosure. The upper arced support structure 332, the lower arced support structure 334, and the chorded bottom 336 are concentric at the focal spot of the X-ray source 501. Since the flexible upper curved anti-scatter toothed metal strips 352 and lower curved anti-scatter toothed metal strips 354 are secured against the upper and lower arced support structures 332 and 334 respectively, the curved anti-scatter toothed metal strips 350 are also concentric at the focal spot of the X-ray source 501. The slots 520 (shown in FIG. 5A) on the curved anti-scatter toothed metal strips 350 and the slot pitch 530 (shown in FIG. 5A), which is the distance between the centers of the two neighboring slots 520, are configured and arranged so that each anti-scatter plate 360 are aligned with the focal spot of the X-ray source 501. In accordance with one exemplary embodiment of the present disclosure, each scintillator element is equally spaced along the chorded bottom 336, the slots 520 on both upper and lower curved anti-scatter toothed metal strips are also evenly distributed along the radial direction of the arced support structure 330.

In accordance with one embodiment of the present disclosure, the DMAS 300 may further include anti-scatter plates 360 and curved anti-scatter toothed metal strips 350; wherein the anti-scatter plates 360 are secured and aligned with the scintillator arrays 412 using the curved anti-scatter toothed metal strips 350; wherein the curved anti-scatter toothed metal strips 350 are aligned and secured to the DMAS arced support structure 330. The curved anti-scatter toothed metal strips 350 are made of flexible metal or other suitable substance; wherein each of two opposite sides 510 of each anti-scatter plate 360 communicates with precise slots 520 of at least two curved anti-scatter toothed metal strips 350 that are aligned along Y-axis as shown in FIG. 5A; wherein the curved anti-scatter toothed metal strips 350 assume the same curvature as the DMAS arced support structure 330; and wherein the combination of the curvature and the precise slots align the anti-scatter plates 360 to the X-ray source 501 as shown in FIG. 5C.

Figure 6:
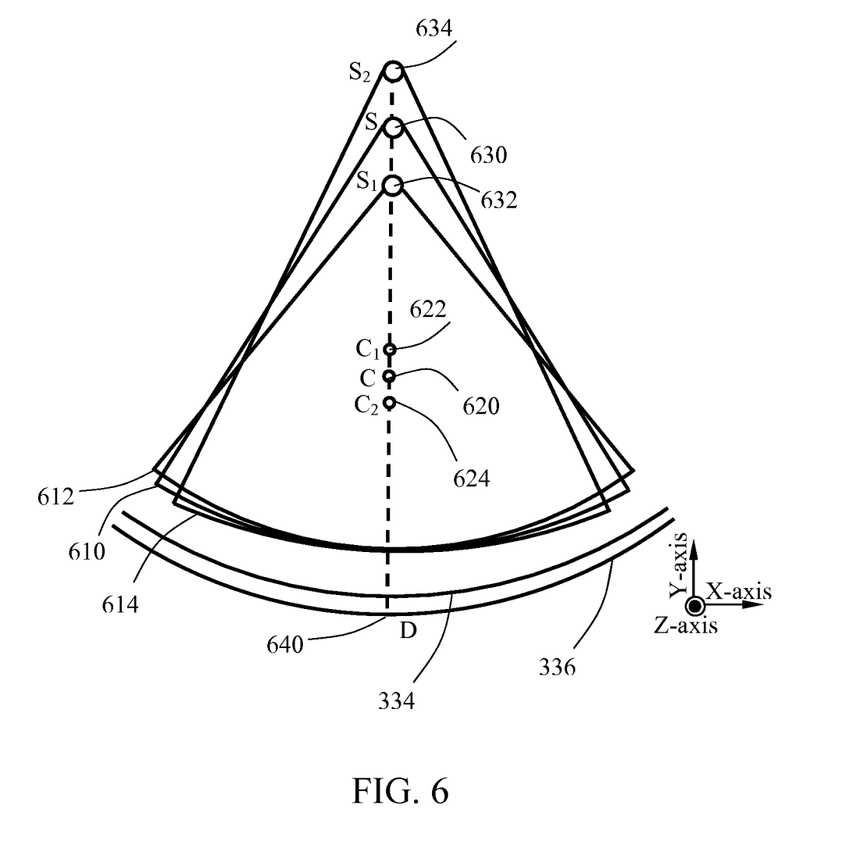
FIG. 6 shows a schematic functional diagram of different multi-slice CT systems using the multi-slice X-ray CT DMAS of different configurations in accordance with one embodiment of the present disclosure.

FIG. 6 shows a schematic functional diagram of different multi-slice CT systems using the configurable multi-slice X-ray CT DMAS 300 in accordance with one embodiment of the present disclosure. In accordance with one embodiment of the present disclosure, a plurality of DMAS modular assemblies 310 are aligned, mounted and secured along the DMAS arced support structure 330 as shown in FIG. 3. The DMAS arced support structure 330 includes a configurable upper arced support structure 610 for supporting and securing the upper curved anti-scatter toothed metal strips, a fixed lower arced support structure 334 for supporting and securing the lower curved anti-scatter toothed metal strips, and a chorded bottom 336 for securing and aligning DMAS modular assemblies. The default configuration of the upper arced support structure 610, the fixed lower arced support structure 334, and the chorded bottom 336 are all concentric at the focal spot of the X-ray source S 630 of a multi-slice X-ray CT system. For different X-ray CT systems of different X-ray source locations, such as $S_1$ 632 or $S_2$ 634, the configurable upper arced support structures are machined to have upper arced support structures 612 and 614 respectively; the upper arced support structure 612 is centered at $S_1$ 632, and the upper arced support structure 614 is centered at $S_2$ 634; the corresponding curved anti-scatter toothed metal strips 350 are also configured and arranged to align the anti-scatter plates 360 to the corresponding X-ray sources; all other components or structures of the DMAS 300 including the lower arced support structure 334, the chorded bottom 336, the lower curved anti-scatter toothed metal strips 354, and the DMAS modular assemblies remain the same as the default X-ray CT system of the X-ray source being at S 630.

Referring to FIG. 6, the DMAS upper arced support structure 610 is centered at the focal spot of the X-ray source S 630 with the focusing distance $R_{SD}$. In this configuration, the X-ray source and the DMAS is rotated with respect to the rotation center C 620. In another configuration, the DMAS 300 can also be arranged and configured to have a focusing distance of $R_{S1D}$ between X-ray source S1 632 with rotation center of C1 622 with the arced support structure 612; in another configuration, the DMAS 300 can also be arranged and configured to have a focusing distance of $R_{S2D}$ between X-ray source S2 634 with rotation center of C2 624 with the arced support structure 614. It will be understood by those skilled in the art that these locations can be varied continuously not only along the line SD but also can be at other locations away from the line SD.

Figure 7:
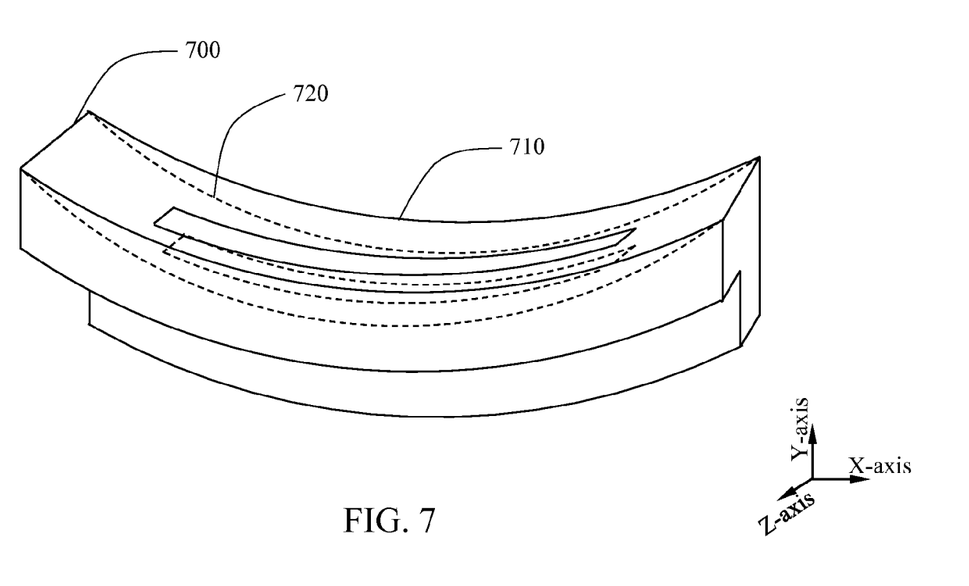
FIG. 7 shows a schematic functional diagram of the multi-slice X-ray CT DMAS arced support structure cast fabricated into two DMAS arced support structures of different focusing distances in accordance with one embodiment of the present disclosure.

FIG. 7 shows a schematic functional diagram of the multi-slice X-ray CT DMAS arced support structure cast 700 fabricated into two different DMAS upper arced support structures of different focusing distances 710 and 720 in accordance with one embodiment of the present disclosure. The DMAS arced support structure cast 700 is cast using, for example aluminum, then to be machined to have a range of pre-determined focusing distances, for example, from 950 mm to 1050 mm. The DMAS upper arced support structure 710, for example, is machined to have focusing distance of 1020 mm, while the DMAS upper arced support structure 720, for example, is machined to have focusing distance of 960 mm. However, the lower arced support structure, the chorded bottom, the DMAS modular assemblies, and the lower curved anti-scatter toothed metal strips remain the same for these two different curvatures of the upper arced support structure.

Figure 8:
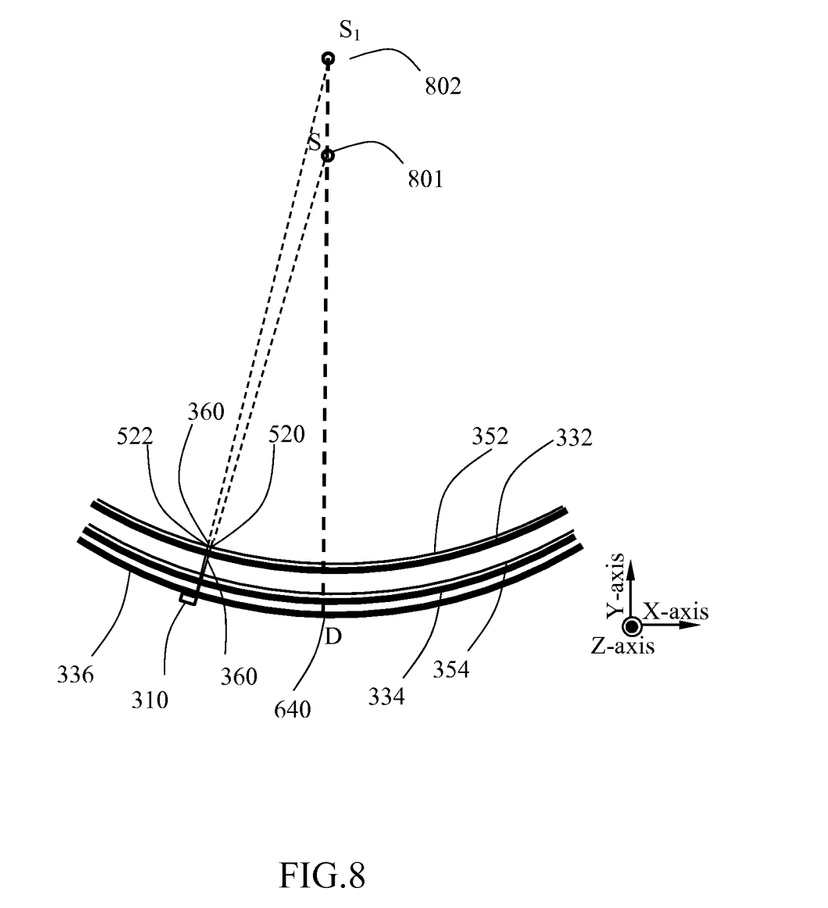
FIG. 8 shows a schematic functional diagram of two different multi-slice CT systems using the configurable DMAS in accordance with one embodiment of the present disclosure.

FIG. 8 shows a schematic functional diagram of two different multi-slice CT systems using the configurable DMAS 300 in accordance with one embodiment of the present disclosure. The arced support structure of the DMAS includes the upper arced support structure 332, the lower support structure 334, and the chorded bottom 336, and they are all concentric at the pre-set X-ray source position S 801. The DMAS modular assemblies 310 are mounted and secured to the chorded bottom 336, aligned to face directly to the X-ray source 801. The lower curved anti-scatter toothed metal strips 354 are secured and mounted on the lower arced support structure 334, concentric at the X-ray source S 801. The upper curved anti-scatter toothed metal strips 352 are secured and mounted on the upper arced support structure 332, concentric at the X-ray source S 801 as well. The precise slots 520 of the curved anti-scatter toothed metal strips 350 are configured and arranged to align each anti-scatter plate to the X-ray source S 801.

In one embodiment of the present disclosure, for an X-ray CT system of different X-ray source location $S_1$ 802, the DMAS only needs to have different upper curved anti-scatter toothed metal strips, and all other components and structures may remain the same. The precise slots 522 of the upper curved anti-scatter toothed metal strips 332 are configured and arranged to align each anti-scatter plate to the X-ray source $S_1$ 802 instead of 801. When all the scintillator element are equally spaced along the chorded bottom 336, the precise slots of the upper and lower curved anti-scatter toothed metal strips are equally spaced for the X-ray source S 801; however, when configured for X-ray source $S_1$ 802, the precise slots 522 of the upper curved anti-scatter toothed metal strips 352 become unevenly spaced in order to align each anti-scatter plate to the X-ray source $S_1$ 802. Because each scintillator element is directly facing the X-ray source S 801, but not directly facing the X-ray source $S_1$ 802, the effective pitches (neighboring scintillator center to center distance) of the scintillators are not constant any more.

In accordance with one embodiment of the present disclosure, the DMAS further includes upper curved anti-scatter toothed metal strips 352 and lower curved anti-scatter toothed metal strips 354; wherein the arced support structure further includes an upper arced support structure 332 for mounting and securing the upper curved anti-scatter toothed metal strips 352, a lower arced support structure for mounting and securing the upper curved anti-scatter toothed metal strips 352, and a chorded bottom 336 for securing the DMAS modular assemblies 310 including scintillator arrays, the photodiode modules, and the digitizing cards; wherein the upper arced support structure 332, the lower arced support structure 334, and the chorded bottom 336 are concentric at a pre-set X-ray source position S 801; wherein the DMAS may further includes anti-scatter plates 360, which are secured and aligned to the X-ray source position S 801 by using precise slots 520 of the upper and lower curved anti-scatter toothed metal strips 354. Since the upper and lower curved anti-scatter toothed metal strips are made flexible materials, they are fit to the curvature of the upper and lower arced support structures, and also concentric at the X-ray source position S 801.

In accordance with one embodiment of the present disclosure, the upper curved anti-scatter toothed metal strips 352 are configured and arranged to align the anti-scatter plates 360 to another X-ray source position $S_1$ 802 that is different from the pre-set X-ray source position S 801 that the upper arced support structure, the lower arced support structure, and the chorded bottom are concentric at.

In accordance with one embodiment of the present disclosure, the DMAS can be arranged and configured for multi-slice X-ray CT systems of different X-ray source focusing distances; and wherein the arced support structure of the DMAS is fabricated from an arced casting of a first radius, for example 1000 mm, within a pre-determined range of radii, for example from 950 mm to 1050 mm, and is then machined to a second radius, for example 1020 mm, that is within the pre-determined range of radii; and wherein the X-ray source focusing distances are the radii of the arced support structure.

In accordance with another aspect of one embodiment of the present disclosure, the detector Z pitch $P_z$, the distance between the centers of two adjacent scintillator elements along Z-axis, is related to CT system's slice width at the center of rotation. The relationship is $W_S=PzR_{SC}/R_{SD}$, where $W_S$ is the slice width at the center of rotation, $R_{SC}$ is the distance between the focal spot S and the center of rotation C, and $R_{SD}$ is the focusing distance between the focal spot S and the DMAS arc D. With fixed detector Z pitch, for different $R_{SD}$, the slice width $W_S$ is the same when $R_{SC}$ is chose so that $R_{SC}/R_{SD}$ is constant. Therefore, the DMAS 300 configured and machined for different focusing distances can have the same slice width for CT systems of different focusing distances.

In accordance with one embodiment of the present disclosure, a multi-slice X-ray Computed Tomography (CT) system may comprises one or more X-ray sources and one or more Data Measurement and Acquisition Systems (DMAS); wherein each DMAS may comprise a plurality of X-ray scintillator arrays for receiving and converting X-ray photons to light photons, a plurality of photodiode modules with the X-ray scintillator arrays being mounted on for converting the light photons to analog signals, a plurality of digitizing cards connected with the photodiode modules for digitizing the analog signals into digital data, one or more motherboards connected with the digitizing cards using digital cables; wherein the motherboards control the digitizing cards for sampling and digitizing the analog signals, and, an arced support structure for mounting and securing the photodiode modules, the digitizing cards, and the motherboards; wherein the arc focuses on one X-ray source of the X-ray CT system and each X-ray scintillator array is configured and arranged to focus on the X-ray source.

In accordance with one embodiment of the present disclosure, the DMAS is arranged and configured to have a first number, for example 46, of digitizing cards for a simultaneous acquisition of a first maximum number of slices, for example 16 slices, of CT images; wherein the DMAS can be later added with a second number, for example 46, of digitizing cards with total number, for example 92, of digitizing cards being the sum of the first number and the second number for a simultaneous acquisition of a second maximum number of slices, for example 32 slices, of CT images; and wherein the sum is no greater than a pre-determined number, for example 92.

In accordance with one embodiment of the present disclosure, a photodiode module for X-ray systems, wherein each of the X-ray systems comprises a plurality of scintillator arrays for receiving and converting X-ray photons to light photons and one or more X-ray sources, comprises a photodiode array for receiving the light photons and converting the light photons to electric charges; a support substrate, to which the photodiode array is precisely mounted; wherein the support substrate also transport the electric charges; and a support plate, which is mounted to the support substrate on the opposite side that the photodiode array is mounted to.

In accordance with one embodiment of the present disclosure, a photodiode module for X-ray systems, wherein the X-ray systems comprise a plurality of scintillator arrays for receiving and converting X-ray photons to light photons and one or more X-ray sources, comprises one or more high-density connectors; a photodiode array; and a support substrate; wherein the photodiode array is precisely mounted to the support substrate; wherein the high-density connectors are precisely mounted to the support substrate; and wherein the analog signals generated by the photodiode array are transported to the high-density connectors; wherein the high-density connectors on the support substrate of the photodiode module have different mated heights along Y-axis; and wherein the high-density connectors are displaced along Z-axis.

While this disclosure has been particularly shown and described with references to the embodiments thereof, it will be understood by those skilled in the art that various changes in form and details may be made therein without departing from the spirit and scope of the disclosure as defined by the following claims. These variations from the embodiment of the present disclosure include but not limited to extending the 32 rows of scintillator array and photodiode array to different numbers, such as 64 rows, 128 rows, 256 rows, and etc.

The invention claimed is:

1. A Data Measurement and Acquisition System (DMAS) for multi-slice X-ray Computed Tomography (CT) systems, wherein each said X-ray CT system includes at least one X-ray source, comprising:
  A. A plurality of X-ray scintillator arrays for receiving and converting X-ray photons to light photons;
  B. A plurality of photodiode modules, to which said X-ray scintillator arrays are mounted for converting said light photons to analog signals;
  C. A plurality of digitizing cards connected with said photodiode modules using high-density connectors, which are not flexible electrical cables or wire-bonded connections, for digitizing said analog signals into digital data;
  D. One or more motherboards connected with said digitizing cards using digital cables; wherein said motherboards control said digitizing cards for sampling and digitizing said analog signals; and, E. An arced support structure for mounting and securing said photodiode modules, said digitizing cards, and said motherboard(s); wherein the arc of said arced support structure focuses on one X-ray source of said X-ray CT system and each said X-ray scintillator array is configured and arranged to focus on said X-ray source;

wherein said DMAS is arranged and configured with a first number of digitizing cards for a first multi-slice X-ray CT system; wherein said DMAS can also be arranged and configured with a second number of digitizing cards for a second multi-slice X-ray CT system; wherein said first number is smaller than said second number; wherein said first multi-slice X-ray CT system and said second multi-slice X-ray CT system are two physically different systems, and said first multi-slice X-ray CT system cannot be reconfigured to said second multi-slice X-ray CT system without physically adding said digitizing cards.

2. The system of claim 1, wherein said DMAS is arranged and configured for multi-slice X-ray CT systems of different X-ray source locations; and wherein said arced support structure of said DMAS is fabricated from an arced casting of a first radius that is within a pre-determined range of radii and is then machined to a second radius that is within said pre-determined range of radii; wherein said first radius and said second radius are different; and wherein said X-ray source location corresponds to said second radius of said arced support structure.

3. The system of claim 1, wherein said DMAS includes anti-scatter plates and curved anti-scatter toothed metal strips; wherein said anti-scatter plates are secured and aligned with said scintillator arrays using said curved anti-scatter toothed metal strips; wherein said curved anti-scatter toothed metal strips are aligned and secured to said arced support structure of said DMAS.

4. The system of claim 3, wherein said curved anti-scatter toothed metal strips are made of flexible metal or other suitable substance; wherein each of two opposite sides of each said anti-scatter plate communicates with precise slots of at least two said curved anti-scatter toothed metal strips that are aligned along Y-axis; wherein each said curved anti-scatter toothed metal strip has the same shape as said arced support structure on which the curved anti-scatter toothed metal strip is placed; and wherein the combination of said curvature and said precise slots align said anti-scatter plates to said X-ray source.

5. The system of claim 1, wherein each said photodiode module comprising,
A. A photodiode array for converting said light photons to said analog signals;
B. A support substrate, to which said photodiode array is precisely mounted; and,
C. A support, which is mounted to said support substrate on the opposite side to which said photodiode array is mounted to.

6. The system of claim 1, wherein each said photodiode module comprising,
A. One or more high-density connectors;
B. A photodiode array for converting said light photons to said analog signals; and,
C. A support substrate;
wherein said photodiode array is precisely mounted to said support substrate; wherein said high-density connectors are precisely mounted to said support substrate; and wherein the analog signals generated by said photodiode array are transported to said digitizing cards via said high-density connectors.

7. The system of claim 6, wherein each said photodiode module further includes combination switches for combining elements of photodiode modules along Z-axis; wherein said analog signals generated by said photodiode array are transported through said combination switches to said high-density connectors.

8. The system of claim 6, wherein each said digitizing card further includes a high-density plug corresponding to one of said high-density connectors of said photodiode modules.

9. The system of claim 8, wherein two or more of said digitizing cards connecting said photodiode module are displaced along Y-axis with all of said high-density connectors of each said photodiode module being of different mated heights.

10. A Data Measurement and Acquisition System (DMAS) for multi-slice X-ray Computed Tomography (CT) systems, wherein each said X-ray CT system includes at least one X-ray source, comprising:
A. A plurality of X-ray scintillator arrays for receiving and converting X-ray photons to light photons;
B. A plurality of photodiode modules, to which said X-ray scintillator arrays are mounted for converting said light photons to analog signals;
C. A plurality of digitizing cards connected with said photodiode modules using high-density connectors, which are not flexible electrical cables or wire-bonded connections, for digitizing said analog signals into digital data;
D. One or more motherboards connected with said digitizing cards using digital cables; wherein said motherboards control said digitizing cards for sampling and digitizing said analog signals; and,
E. An arced support structure for mounting and securing said photodiode modules, said digitizing cards, and said motherboard(s); wherein the arc of said arced support structure focuses on one X-ray source of said X-ray CT system and each said X-ray scintillator array is configured and arranged to focus on said X-ray source;

wherein each of said photodiode modules includes combination switches for combining elements of photodiode modules along Z-axis when enabled and for passing through said analog signals only when disabled; wherein said DMAS can be arranged and configured with a first number of digitizing cards for a first multi-slice X-ray CT system and with said combination switches on said photodiode modules being enabled or being disabled; wherein said DMAS can also be arranged and configured with a second number of digitizing cards for a second multi-slice X-ray CT system and with said combination switches on said photodiode modules being disabled; wherein said first number is smaller than said second number; wherein said first multi-slice X-ray CT system and said second multi-slice X-ray CT system are two physically different systems, and said first multi-slice X-ray CT system cannot be reconfigured to said second multi-slice X-ray CT system without physically adding said digitizing cards.

11. A Data Measurement and Acquisition System (DMAS) for multi-slice X-ray Computed Tomography (CT) systems, wherein each said X-ray CT system includes at least one X-ray source, comprising:
A. A plurality of X-ray scintillator arrays for receiving and converting X-ray photons to light photons;
B. A plurality of photodiode modules, to which said X-ray scintillator arrays are mounted for converting said light photons to analog signals;

C. A plurality of digitizing cards connected with said photodiode modules using high-density connectors, which are not flexible electrical cables or wire-bonded connections, for digitizing said analog signals into digital data;

D. One or more motherboards connected with said digitizing cards using digital cables; wherein said motherboards control said digitizing cards for sampling and digitizing said analog signals; and, E. An arced support structure for mounting and securing said photodiode modules, said digitizing cards, and said motherboard(s); wherein the arc of said arced support structure focuses on one X-ray source of said X-ray CT system and each said X-ray scintillator array is configured and arranged to focus on said X-ray source;

wherein said DMAS further includes upper curved anti-scatter toothed metal strips and lower curved anti-scatter toothed metal strips; wherein said arced support structure further includes an upper arced support structure for mounting and securing said upper curved anti-scatter toothed metal strips, a lower arced support structure for mounting and securing said lower curved anti-scatter toothed metal strips, and a chorded bottom for securing said scintillator arrays, said photodiode modules, and said digitizing cards; wherein said upper arced support structure, said lower arced support structure, and said chorded bottom are concentric at a first position; wherein each said curved anti-scatter toothed metal strip has the same shape as said arced support structure on which the curved anti-scatter toothed metal strip is placed; wherein said DMAS may further include anti-scatter plates, which are secured and aligned to said X-ray source position by using precise slots of said upper and lower curved anti-scatter toothed metal strips; wherein said X-ray source is located at a second position, which is different from said first position, wherein said upper anti-scatter toothed metal strips and said lower anti-scatter toothed metal strips are configured and arranged to align said anti-scatter plates to said second position; wherein said second position is only determined by the arrangement of said precise slots of said upper and lower curved anti-scatter toothed metal strips, and is not determined by the shapes of said upper arced support structure, said lower arced support structure, and said chorded bottom.

* * * * *